United States Patent [19]

Wilkins et al.

[11] Patent Number: Plant 6,815

[45] **Date of Patent: * May 23, 1989**

[54] KIWIFRUIT PLANT

[76] Inventors: Marcus J. Wilkins; Jan Wilkins, both of Pongakawa, Warwick Farm R.D. 6, Te Puke, New Zealand

[ * ] Notice: The portion of the term of this patent subsequent to Aug. 11, 2004 has been disclaimed.

[21] Appl. No.: 844,907

[22] Filed: Mar. 27, 1986

[51] Int. Cl.[4] ..... A01H 5/03

[52] U.S. Cl. ..... Plt./33

[58] Field of Search ..... Plt./33

*Primary Examiner*—Robert E. Bagwill

*Attorney, Agent, or Firm*—Townsend & Townsend

[57] ABSTRACT

A new and distinctive variety of kiwifruit is described. This fruit is a sport or mutation of the 'Hayward' variety. It is distinguished by its long and substantially cylindrical fruit. It was first observed in a kiwifruit orchard in Pongakawa, New Zealand.

1 Drawing Sheet

The present invention relates to a new and distinctive kiwifruit cultivar having a large and generally cylindrically shaped fruit. More particularly, the new cultivar is designated 'Wilkins Super' and is a mutation or sport from the 'Hayward' variety.

After the new variety was discovered, it was asexually reproduced in 1979 on Petitioners' property at Pongakawa, New Zealand, by grafting onto rootstock of the 'Bruno' variety. The fruit was first observed on the reproduced plants in 1982. 'Wilkins Super' has been tested with favorable results at two sites in a New Zealand government research orchard at Te Puke, New Zealand. This testing, which has been conducted under strict supervision, demonstrated that the reproduced plants have the same characteristics as the original plant from which graftwood was taken.

The invention may be more fully understood by having reference to the accompanying photographic color reproductions, wherein.

DETAILED DESCRIPTION

Fruit and Fruiting

The distinctive characteristics of this new kiwifruit cultivar described in detail below have been observed since its discovery in 1982.

Figure 1:
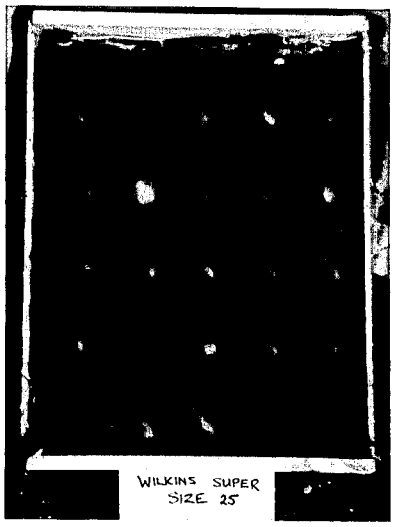
FIG. 1 is a box of fruit of 'Wilkins Super'.
Figure 3:
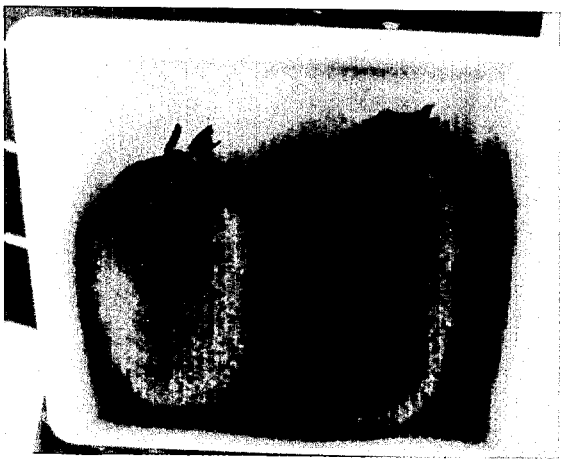
FIG. 3 shows a typical mature fruit of the 'Wilkins Super' on the right variety next to a 'Hayward' fruit of a similar maturity.
Figure 2:
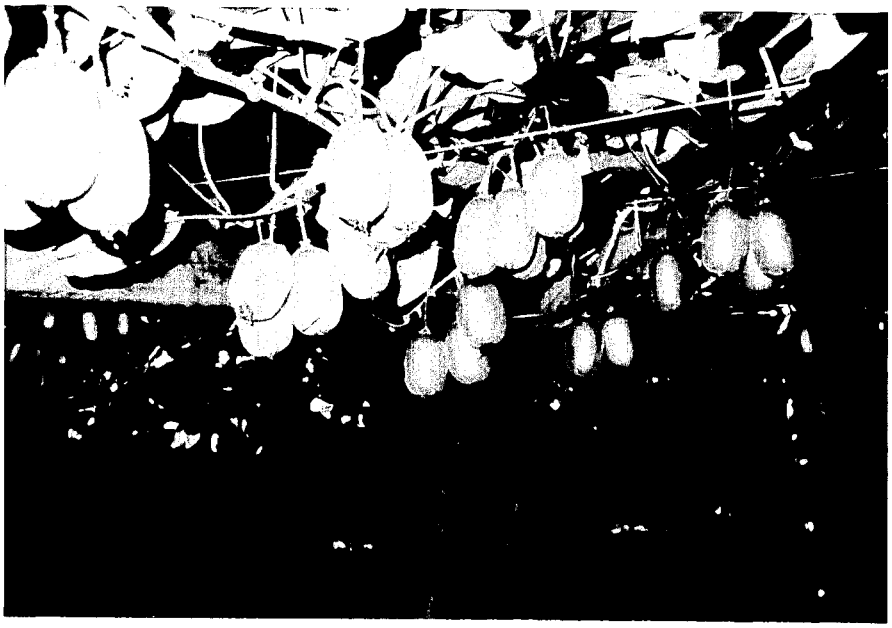
FIG. 2 shows a typical collection of mature fruit on a vine in an orchard.

'Wilkins Super' is distinct from the 'Hayward' variety in its fruit shape. As is illustrated in FIG. 3 'Wilkins Super' is notably longer. Other fruit characteristics such as hair density, color and asymmetry of fruit shape are similar to that of 'Hayward'.

'Wilkins Super' is different from two other "long-shaped" kiwifruit, 'Bruno' and 'Gracie' in a number of characteristics set out in Table 1.

The distinctive characteristics of this new kiwifruit cultivar described in detail below have been observed since its discovery in 1982.

'Wilkins Super' is distinct from the 'Hayward' variety in its fruit shape. As is illustrated in FIG. 3 'Wilkins Super' is notably longer. Other fruit characteristics such as hair density, color and asymmetry of fruit shape are similar to that of 'Hayward'.

'Wilkins Super' is different from two other "long-shaped" kiwifruit, 'Bruno' and 'Gracie' in a number of characteristics set out in Table 1.

The color designations hereinafter set forth are according to the Munsell Color System - Nickerson Color Fan.

TABLE 1

| Differences from 'Bruno' | |
|---|---|
| 'Bruno' | 'Wilkins Super' |
| 1. Dormant cane bark color dark, purplish brown (10 R 4/4). | Cane bark color lighter, yellow/green/brown (5 YR 5/2). |
| 2. Bud surface flat. | Bud surface convex. |
| 3. Bud break and fruitfulness high. | Bud break and fruitfulness. |
| 4. Flower petals flat, free. | Petals involute, overlapping. |
| 5. Style curved tip only. | Style strongly curved in middle. |
| 6. Fruits more symmetrical, hairs reddish brown (5 YR 4/8). | Fruits asymmetrical, hairs dark brown (7, 5 YR 7/6). |
| 7. Fruit core small. | Fruit core large. |
| **Differences from 'Gracie'** | |
| 'Gracie' | 'Wilkins Super' |
| 1. Leaves flat, horizontal. Petiole hairs few long, brown (7, 5 YR 7/6). | Leaves flat, downturned. Petiole hairs short light red (5 YR 7/8). |
| 2. Petals recurved, corolla revolute and overlapping. Hairs on stylar base few short. | Petals cupped, corolla involute and overlapping. Hairs on stylar base dense and long. |
| 3. Fruit shape obovoid with sloped shoulders. | Fruit shape oblong with prominent shoulders. |

A comparison of measurements of length and of length and width ratios between 'Wilkins Super' and 'Hayward' is set out below in Table 2. The measurements were made on a sampling of at least ten fruit from five vines.

TABLE 2

| Measurements of length/width ratios | | | |
|---|---|---|---|
| | Av. length (inches) | Ratio length width (max) | Ratio width (max) length |
| 'Hayward' | 2.63 | 1.18 | 0.849 |
| 'Wilkins Super' | 3.16 | 1.53 | 0.651 |

The fruit is of a large size as compared to the 'Hayward' variety. It is substantially cylindrical in shape but has a elliptical cross-section typical of the 'Hayward' variety. The skin color is greenish/brown (5 Y 6/4), also typical of 'Hayward'. It has a silky type of hair of sparse density. The length of the hair is long and in this characteristic is distinguishable from 'Hayward'. The hairs at harvest are medium brown (7, 5 YR 7/6). The stylar end is flat. The diameter of the columella (median cross-section) is medium, in cross-section the columella is elliptical. The green color of the flesh is a medium green. (2 5 GY 7/8).

The time of maturity for harvest is late. This time is reached when the average soluble solids content of a sample of at least ten fruit from five vines (measured using a refractometer) reaches 6.2% ss.

The storage life in cool store of 'Wilkins Super' is comparable with that of 'Hayward'. The storage life of 'Hayward' is notably longer than that of other kiwifruit varieties.

Plant

The plant demonstrates a female sex expression. It has a medium vigor.

A young shoot was observed two month after flowering on undernotes of four to eight inches on the tip of growing shoots. A medium anthocyanin (5 YR 4/10) coloration of hairs was observed. The hairs were of medium density as in the 'Hayward' variety and of short length. The anthocyanin (5 YR 4/10) coloration in the leaf axil was weak as in the 'Hayward' variety.

The central third of a stem of a dormant cane was observed after leaf fall. The color was reddish/brown (5 YR 5/2) as in 'Hayward'. The "russet" on the bark was longitudinal. The number of lenticels was few and of medium conspicuousness. The wood bud support was small and the leaf scar was medium as in 'Hayward'.

A first fully developed leaf was observed from the growth tip. It had a generally oblate blade and cuspidate tip. The angle of the apical part was obtuse. The shape at the base was touching. The upper surface of the leaf had a medium glossiness. The density of hair on the main veins of the upper side of the leaf was medium as in 'Hayward'. The density of hair between the main veins on the upper side of the leaf was sparse. The density of hair on the main veins on the lower side of the leaf was medium. The density of stellate hair between the main veins on the lower side of the leaf was dense. The anthocyanin coloration (5 YR 4/10) of the petiole was weak.

A mature leaf was observed near the base of the current season's growth on mature but not old leaves. The green color (7, 5 GY 4/4) on the other side was dark. The blistering of the upper side was medium as in the 'Hayward' variety. The spiney ciliation on the margin was absent. The glossiness of the upper surface was medium. The time of leaf fall was late.

The time of the beginning of a flowering was late as in the 'Hayward' variety. The predominant number of flowers was one as in the 'Hayward' variety. The length of the pedicel was medium having short hairs. The length of the sepal of the flower was medium and of a cream/brown color (2,5 Y 7/6). The length of the petal was medium with a length/width ratio of petal being less than twice as long as broad. The petals were overlapping. The petals had a smooth surface with a cut (involute) curvature and no shoulder. The many styles were curved above the middle and semi-erect. There were tufts or hairs present at the base of these styles as in the 'Hayward' variety. There were many stemens present.

We claim:

1. The new and distinct variety of kiwifruit plant herein described and illustrated, and identified by the characteristics enumerated above.

* * * * *